United States Patent [19]

Gazzani

[11] 4,371,518

[45] Feb. 1, 1983

[54] CARRIERS FOR SPERMICIDAL SUBSTANCES

[75] Inventor: Giovanni Gazzani, Appiano Gentile, Italy

[73] Assignee: Crinos Industria Farmabiologica S.p.A., Villa Guardia, Italy

[21] Appl. No.: 267,393

[22] Filed: May 26, 1981

[30] Foreign Application Priority Data

Jun. 20, 1980 [IT] Italy ............................... 22910 A/80

[51] Int. Cl.³ .................... A61K 31/09; A61K 31/74; A61K 47/00
[52] U.S. Cl. ........................................ 424/78; 424/79; 424/258; 424/291; 424/317; 424/329; 424/341; 424/DIG. 14
[58] Field of Search .......... 424/78, 361, 341, DIG. 14

[56] References Cited

U.S. PATENT DOCUMENTS

| | | | |
|---|---|---|---|
| 4,187,286 | 2/1980 | Marcus | 424/44 |
| 4,242,359 | 12/1980 | Cooper et al. | 424/325 |
| 4,268,501 | 5/1981 | Konno et al. | 424/80 |

OTHER PUBLICATIONS

Chemical Abstracts 75:40316n (1971).
Chemical Abstracts 75:143970a (1971).

*Primary Examiner*—Leonard Schenkman
*Attorney, Agent, or Firm*—Browdy and Neimark

[57] ABSTRACT

The use of crosslinked polysaccharides as vehicles for spermicidal substances in compositions used for local contraception is described. The crosslinked polysaccharide (e.g. a modified dextran) is admixed with the spermicidal agent and formed into tablets for vaginal applications; the dextran swells in contact with the vaginal secretion and includes the seminal liquid thus bringing into contact the sperm cells with the spermicidal substances dispersed therein.

5 Claims, No Drawings

CARRIERS FOR SPERMICIDAL SUBSTANCES

BACKGROUND OF THE INVENTION

The present invention relates to novel carriers or vehicles for spermicidal substances and in particular to the use of modified dextrans as novel vehicles of spermicidal substances in compositions used in local contraception.

It is known that local contraception with chemical agents is based on the use of spermicidal substances contained in tablets, suppositories, creams, solutions for spray applications, etc., which immobilize or kill the sperm cells, preventing them from running up through the female birth canal and avoiding thus a meeting with the ovule.

In reality the use of hitherto known preparations has certain limits mainly due to the difficulty of satisfactorily bringing into contact the spermicidal agents with the sperm cells. It can occur in fact that at the time of ejaculation, a portion of the sperm is directly sucked into the cervical canal and runs up through it without stopping in the vagina where the spermicidal substances are staying. This is one of the reasons for the failures which are met with by such an contraceptive method.

Also the use of sparkling, foaming and surfactant substances which promote an even dispersion of the spermicidal agents in the vagina has not allowed to notably improve the trust index of the local contraceptive agents, which are therefore the least reliable anitfecundative methods among the ones not based on the menstrual cycle.

SUMMARY OF THE INVENTION

In order to discover novel, more or less inert, vehicles suitable to give a higher effectiveness to the spermicidal substances for local applications, some substances have been tested which have been used as inert vehicles or carriers in the chemical field. During these tests, the inventors have found that some modified dextrans which are endowed with the property of quickly absorbing remarkable amounts of liquids can be usefully employed as new vehicles in compositions containing spermicidal substances.

The utility of using the novel vehicles according to the present invention in anhydrous formulations containing spermicidal agents is based on the property of said dextrans of attracting and rapidly absorbing high amounts of liquids, in particular aqueous liquids, so that they swell by coming into contact with the male seminal liquid and vaginal secretions and form a bulky and soft gel which causes a more complete and sure contact between the spermicidal substances which are dispersed in the bulky mass and the thus included sperm cells. The softness characteristics of the thus formed gel are, on the other hand, such as not to compromise the normal vaginal lubrication as well as the elasticity and turgor of the mucoses.

The novel vehicle according to the present invention consists of dextrans treated with epichlorohydrin which give rise to glycerilenic cross-links having crossed structures of the type:

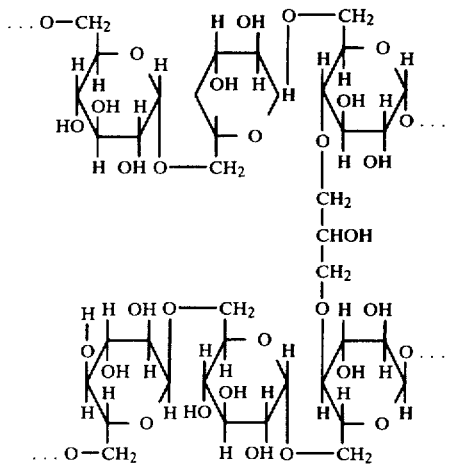

wherein one or more hydroxyl groups of the individual rings can be etherified with functional groups such as carboxyalkyl, sulphoalkyl, dialkylaminoethyl groups, quaternary ammonium groups, and the like.

These substances are already known and commercially available under various trade names (for instance Sephadex), and marked by abbreviations which differentiate them according to their characteristics and are used in the chemical field, for instance as carriers for ionic exchangers in gel-filtration and chromatography. Such substances are solids, generally in the form of microspheres, insoluble in water but highly hydrophilic and capable of absorbing remarkable amounts of aqueous liquids with subsequent swelling and formation of bulky and soft gels, the absorbing power thereof depending on the number and position of the cross-links and/or the type of substituents which were introduced in the macromolecule.

Substances as above described which can advantageously be used according to the present invention comprise modified unsubstituted dextrans (G) or dextrans substituted with carboxymethyl (CM), sulphopropyl (SP), diethylaminoethyl (DEAE), diethyl-(2-hydroxypropyl)-ethylammonium (QAE) groups, whose absorbing power, as based on the seminal liquid, is at least 10 ml/g, preferably 20–40 ml/g.

The said modified dextrans can be used as adjuvating vehicles for already known spermicidal agents in concentrations at which the latter are active. Examples of spermicidal agents which can be used in connection with the novel vehicles according to the present invention are nonylphenoxypolyethoxyethanol, 8-hydroxyquinoline, lactic acid, phenylmercuric nitrate or borate, benzethonium chloride, benzalkonium chloride, cetyl-pyridinium chloride, alone or in mutual combinations.

The application form of the local contraceptive according to the present invention is preferably a tablet having preferably a reduced thickness and lenticular section in order to increase its contacting surface, which tablet can be formulated, besides with the above described modified dextran and spermicidal agent, also with further usual vehicles, such as microcrystalline cellulose, lactose, mannitol, talc, magnesium trisilicate, polyglycols and the like.

The amount of modified dextran for each tablet can be changed according its adsorbing power in the range from 0.3 to 1.8 g based on weight/volume and in the case of a high absorbing power equal to at least 40 ml/g, it is preferably from 0.3 to 0.6 g, which amounts allow to absorb with a good margin of safety the sperm ejected in a single ejaculation. The final weight of the tablet obviously depends mainly on the amount of modified dextran used and can change accordingly between 0.6 and 2.5 g. A particularly preferred composition according to the present invention comprises for instance 0.05 g nonylphenoxypolyethoxyethanol and 0.45 g unsubstituted modified dextrane in addition to other usual vehicles.

DESCRIPTION OF A PREFERRED EMBODIMENT

The present invention is now more particularly explained on the basis of an embodying example which is in no way to be construed in a limiting sense.

EXAMPLE 1

For the preparation of 1000 tablets each weighing 1 g:
nonylphenoxypolyethoxyethanol: 50 g
modified dextran: 450 g
microcrystalline cellulose: 450 g
polyglycol 6000: 50 g
were used.

Nonylphenoxypolyethoxyethanol and polyglycol 6000 were mixed together and heat-melted under stirring. The waxy mass was allowed to cool and transferred into a granulating mill provided with a sieve, then the modified dextran having an absorbing power of 40 ml/g was added. The mass is mixed for some minutes and the microcrystalline cellulose is then added under continuous mixing until complete homogenization. The obtained mass is passed to a tablet press which gives tablets having a lenticular section and weighing 1 g.

In order to ascertain the absorbing ability of the thus obtained tablets with respect to water or biological liquids, a tablet is placed on a scale pan and the liquid to be tested is gradually added at the center of the tablet by means of a pipette; the addition of the liquid is stopped as soon as the swollen tablet does no longer absorb the liquid which tends therefore to spread on the scale pan. At this time the weighing is repeated and the amount of the absorbed liquid is determined by difference.

The absorbing and spermicidal or spermostatic activity of the tablets comprising a modified dextran according to the present invention was confirmed in vitro by acting according to the following procedure: a fragment of a tablet is placed on a slide and a drop of seminal liquid picked up by a pipette is placed near the fragment so as to avoid direct contact between the tablet and the liquid. The slide is transferred under a microscope so that the field of vision comprises the area of the sperm drop which is close to the tablet fragment. Always observing the field of vision of the microscope, the tablet fragment is shifted at this time by means of a small spatula in order to contact it with the seminal liquid, thus evaluating both the absorption velocity of the liquid and the movement of the sperm cells when they are within the tablet.

Besides a particularly quick absorption of the spermatic liquid, an immediate stopping of the movements of the sperm cells sucked up by the swollen tablet can be observed.

The practical use of the spermicidal formulations according to the present invention takes place by introducing into the vagina, for example, a tablet prior to the sexual intercourse.

Although the present invention has been explained on the basis of a particularly preferred embodying example, it is obvious that changes and/or alternations can be introduced therein without departing therefore from the protective scope of the invention; in particular, as the swelling vehicle any other hydrophilic, polymeric, pharmacologically acceptable substance can thus be used.

What we claim is:

1. A spermicidal composition for topical use containing an active amount of a known spermicidal agent dispersed in a suitable vehicle, wherein said vehicle consists of a water insoluble hydrophilic crosslinked dextran in an amount sufficient to have an absorptive capacity greater than the amount of sperm which can be ejaculated in a single ejaculation.

2. The composition according to claim 1, wherein said crosslinked dextran is a dextran modified with epichlorohydrin, or a dextran modified with epichlorodydrin in which some of the existing hydroxy groups have been etherified with functional groups, such as carboxyalkyl, sulphoalkyl, dialkylaminoalkyl or quaternary ammonium groups.

3. The composition according to claim 2, wherein said functional groups are carboxymethyl, sulphopropyl, diethylaminoethyl or diethyl-(2-hydroxypropyl)-ethylammonium groups.

4. A composition according to any one of claims 1, 2 or 3, wherein said composition is in the form of a tablet for vaginal application.

5. A composition in accordance with claim 4, wherein said vehicle is present within the range of 0.3 to 1.8 grams per tablet.

* * * * *